United States Patent
Stav et al.

(10) Patent No.: US 12,000,788 B1
(45) Date of Patent: Jun. 4, 2024

(54) INLINE DETECTION OF GYPSUM PANEL CALCINATION

(71) Applicants: Gold Bond Building Products, LLC, Charlotte, NC (US); MALCAM Ltd., Tel Aviv (IL)

(72) Inventors: Eli Stav, Charlotte, NC (US); Danny Moshe, Ramat HaSharon (IL)

(73) Assignees: Gold Bond Building Products, LLC, Charlotte, NC (US); MALCAM Ltd., Tel-Aviv (IL)

( * ) Notice: Subject to any disclaimer, the term of this patent is extended or adjusted under 35 U.S.C. 154(b) by 469 days.

(21) Appl. No.: 17/145,519

(22) Filed: Jan. 11, 2021

Related U.S. Application Data (60) Provisional application No. 62/959,426, filed on Jan. 10, 2020.

(51) Int. Cl.
*G01N 22/04* (2006.01)
*C01F 11/46* (2006.01)
(Continued)

(52) U.S. Cl.
CPC .............. *G01N 22/04* (2013.01); *C01F 11/46* (2013.01); *C04B 11/00* (2013.01); *C01P 2006/82* (2013.01); *C04B 2111/0062* (2013.01)

(58) Field of Classification Search
CPC ......... G01N 22/04; C01F 11/46; C04B 11/00; C04B 2111/0062; C01P 2006/82
See application file for complete search history.

(56) References Cited

U.S. PATENT DOCUMENTS

| | | |
|---|---|---|
| 5,621,330 A | 4/1997 | Greenwald et al. |
| 5,845,529 A | 12/1998 | Moshe et al. |
| | (Continued) | |

FOREIGN PATENT DOCUMENTS

| | | |
|---|---|---|
| IL | 119537 | 1/2003 |
| WO | WO0014552 | 3/2000 |

*Primary Examiner* — Christopher P McAndrew
*Assistant Examiner* — Zannatul Ferdous
(74) *Attorney, Agent, or Firm* — Dority & Manning, P.A.

(57) ABSTRACT

The present invention is directed to a method of determining a free moisture content and/or a degree of calcination of a gypsum panel. The method comprises the following: (a) transmitting a microwave beam through at least a first portion of the gypsum panel, such that said microwave beam is a transmitted microwave beam; (b) receiving the transmitted microwave beam to form a received microwave beam; (c) determining a phase shift and an attenuation from the received microwave beam; (d) repeating steps (a) to (c) for at least a second portion of the gypsum panel, such that a plurality of phase shifts and a plurality of attenuations is obtained; (e) using at least one empirical factor to correct the plurality of attenuations, producing a plurality of corrected attenuations; (f) calculating a raw moisture content of the gypsum panel from the corrected attenuations wherein the raw moisture content comprises a raw free moisture content and a raw crystal moisture content; (g) using a calibration factor to correct the plurality of phase shifts, producing a plurality of corrected phase shifts; (h) determining a density of the gypsum panel from the corrected phase shifts; and (i) calculating a final moisture content of the gypsum panel from the density and from the raw moisture content wherein the final moisture content comprises a final free moisture content and a final crystal moisture content.

16 Claims, 10 Drawing Sheets

(51) Int. Cl.
*C04B 11/00* (2006.01)
*C04B 111/00* (2006.01)

(56) References Cited

U.S. PATENT DOCUMENTS

| | | | | |
|---|---|---|---|---|
| 6,025,724 | A | * | 2/2000 | Moshe .................... G01N 22/04 |
| | | | | 324/634 |
| 6,107,809 | A | * | 8/2000 | Moshe .................... G01N 33/02 |
| | | | | 324/637 |
| 6,111,415 | A | | 8/2000 | Moshe |
| 6,463,794 | B1 | | 10/2002 | Moshe et al. |
| 6,476,619 | B1 | * | 11/2002 | Moshe ................. G01N 33/362 |
| | | | | 324/636 |
| 7,378,855 | B2 | | 5/2008 | Moshe |
| 10,620,052 | B2 | * | 4/2020 | Lash ....................... G01N 25/72 |
| 2003/0222657 | A1 | * | 12/2003 | Biernacki .............. G01N 22/00 |
| | | | | 324/637 |
| 2003/0222658 | A1 | * | 12/2003 | Schajer ................. G01N 22/00 |
| | | | | 324/639 |
| 2004/0239338 | A1 | * | 12/2004 | Jonsson ................ G01N 22/04 |
| | | | | 324/642 |
| 2005/0057263 | A1 | | 3/2005 | Moshe et al. |
| 2013/0330532 | A1 | * | 12/2013 | Dierschke ................ C08K 3/26 |
| | | | | 521/181 |

* cited by examiner

INLINE DETECTION OF GYPSUM PANEL CALCINATION

RELATED APPLICATIONS

This application claims filing benefit of U.S. Provisional Patent Application No. 62/959,426 having a filing date of Jan. 10, 2020, which is hereby incorporated by reference in its entirety.

BACKGROUND OF THE INVENTION

Gypsum panels are commonly used as building materials. These panels include a gypsum core surrounded by a facing material, such as a paper facing material, a non-woven facing material, and/or a polymeric facing material. The panels are typically manufactured using a continuous process, in which a gypsum slurry is deposited and sandwiched between a lower and upper sheet of facing material. Typically, the gypsum slurry is applied on to a continuously advancing lower sheet of facing material, and a continuously advancing upper sheet of facing material is applied over the gypsum slurry. The gypsum slurry and sheets of facing material may pass between parallel upper and lower forming plates or rolls, which shape a continuous length of the gypsum panel material into a desired thickness and width. The gypsum panels are cut to the desired length, for example at the knife section of the process, and then dried in a dryer or kiln. Thereafter, the ends of the panels are trimmed to the desired length and bundled together for transfer or distribution.

Throughout the drying process, excess (free) water is evaporated or removed from the gypsum panels. The objective of the drying is to dry the free water from the panel without affecting the combined water or crystal water of the gypsum, for example as calcium sulfate dihydrate. However, depending on the temperature, moisture, line speed and other parameters, the gypsum may undergo some degree of calcination, which can affect the properties of the dry panel. In particular, during calcination, part of the calcium sulfate dihydrate may be converted to calcium sulfate hemihydrate by the removal of at least part of the crystal water resulting in partial calcination of the gypsum at the paper/core interface and/or to some degree also in the core. In some instances, such calcination may negatively affect the properties of the panel thereby requiring remedial action. While methods may exist to detect the free water content of gypsum panels, there is still room for improvement. In particular, there is a need for an inline method for determining the degree of calcination, such as a volumetric determination, of the gypsum and/or the free water/combined water content of the gypsum panels after drying in the dryer.

SUMMARY OF THE INVENTION

In accordance with one embodiment of the present invention, a method of determining a free moisture content and/or a degree of calcination of a gypsum panel. The method comprises: (a) transmitting a microwave beam through at least a first portion of the gypsum panel, such that the microwave beam is a transmitted microwave beam; (b) receiving the transmitted microwave beam to form a received microwave beam; (c) determining a phase shift and an attenuation from the received microwave beam; (d) repeating steps (a) to (c) for at least a second portion of the gypsum panel, such that a plurality of phase shifts and a plurality of attenuations is obtained; (e) using at least one empirical factor to correct the plurality of attenuations, producing a plurality of corrected attenuations; (f) calculating a raw moisture content of the gypsum panel from the corrected attenuations wherein the raw moisture content comprises a raw free moisture content and a raw crystal moisture content; (g) using a calibration factor to correct the plurality of phase shifts, producing a plurality of corrected phase shifts; (h) determining a density of the gypsum panel from the corrected phase shifts; and (i) calculating a final moisture content of the gypsum panel from the density and from the raw moisture content wherein the final moisture content comprises a final free moisture content and a final crystal moisture content.

Other features and aspects of the present invention are set forth in greater detail below.

BRIEF DESCRIPTION OF THE DRAWINGS

The invention will now be described, by way of example, with reference to the accompanying drawings, in which.

DETAILED DESCRIPTION

It is to be understood by one of ordinary skill in the art that the present discussion is a description of exemplary embodiments only, and is not intended as limiting the broader aspects of the present invention.

Generally speaking, the present invention is directed to a method for determining the properties of a gypsum panel. In particular, these properties may include the degree of calcination and/or the moisture content, for instance upon drying. In one embodiment, the method may allow for determining the degree of calcination as a result of the drying. In another embodiment, the method may allow for determining the moisture content of the gypsum panel. In turn, by making such determinations inline, remedial action may be undertaken if necessary. For instance, a higher than desired degree of calcination and/or moisture content may negatively affect the gypsum panel properties. These properties may include, but are not limited to, the bond strength between the facing material and the gypsum core, the panel strength, shear, nail pull strength, flexural strength, core hardness, edge hardness, etc.

In a typical gypsum panel manufacturing process, gypsum, such as natural gypsum or synthetic gypsum, is formulated into a slurry including water and other additives. Natural gypsum is typically mined. Meanwhile, synthetic gypsum is typically a by-product from a flue-gas desulfurization process. The additives utilized in forming the gypsum slurry may include, but are not limited to, setting accelerants, set retarders, water repellency materials, dispersants, surfactants, foaming agents, strength enhancers, starches, silicone, waxes, celluloses, and reinforcing materials such as organic or inorganic fibers and fillers such as sand, aggregates, vermiculite, glass fibers, and the like.

In general, the raw gypsum employed for making the panel may be composed primarily of calcium sulfate dihydrate, which has the chemical formula $CaSO_4 \cdot 2H_2O$. Prior to formation of the slurry, the raw gypsum may undergo calcination to form calcium sulfate hemihydrate, which has the chemical formula $CaSO_4 \cdot \frac{1}{2}H_2O$. Other phases of $CaSO_4$ may also be present in a low amount in the calcined gypsum, such as insoluble anhydrite, and/or uncalcined gypsum. Calcined gypsum, also referred to as stucco, is typically prepared by heating pulverized uncalcined gypsum in a mill such as a kettle, rotary kiln, roller mill, impact mill, or other devices or simultaneously heating and pulverizing uncalcined gypsum in a mill to yield calcium sulfate hemihydrate and water vapor. The calcined gypsum has the desirable property of being chemically reactive with water which allows the gypsum to set when the two are mixed together. Such setting allows for the conversion of the calcium sulfate hemihydrate to calcium sulfate dihydrate. In addition, this setting allows for the gypsum panel to have the desired mechanical properties and characteristics.

Upon obtaining the calcined gypsum, it is mixed with water and other additives as mentioned above for forming the gypsum slurry. The gypsum slurry is then deposited onto a first sheet of facing material that is conveyed on a conveyor assembly. In addition, a second sheet of facing material is placed on the gypsum slurry thereby sandwiching the gypsum slurry between the first and second sheets of facing material.

The facing material may include paper or a paperboard material, a woven or non-woven material including fibers and/or filaments, and/or a polymeric material. A paper or paperboard facing material may include virgin or recycled pulp fibers. Such facing material may also be a single-ply material or a multi-ply material. If the facing material is a multi-ply material, the outward and middle plies of the multi-ply material may be sized or treated with starches, resins, or other additives to provide water repellency and control absorption of paints and sealers while the inward ply of the multi-ply material may be treated or untreated, so long as the gypsum core can readily adhere to the facing material. In particular, the sizing material may include alkenyl succinic anhydrite, alkyl ketene dimer, or mixtures thereof. In addition, the paper facing material should have sufficient permeability to allow for water vapor to pass through when drying the gypsum panel in the oven or kiln.

In addition or as an alternative to paper or paperboard facing materials, woven or non-woven materials including fibers and/or filaments may be used as a facing material. The facing material may take the form of a woven or non-woven fabric or mesh such as a woven mesh or scrim, a non-woven mesh, a non-woven pervious mesh or mat, or the like. Suitable fibers or filaments include fiberglass resins, thermoplastic materials, thermoset materials, and the like. A woven facing material may be formed by knitting or weaving one or more types of fibers or filament. A non-woven facing material may be formed by gluing or fusing chopped strand or staple fibers together with a resinous binder or other adhesive. The fibers in a non-woven facing material may be either randomly distributed or orientated. Exemplary fibers or filaments include glass, olefins, aramid resins, vinyls, polyesters, nylon, cellulosic fiber, and the like. The fibers or filaments may be coated with an alkali resistant material such as an epoxy resin to protect the fibers from alkalinity of the cementitious core material. A woven or non-woven facing material may also be formed from an inorganic material such as basalt, metal alloys, asbestos, alumina, zirconia, and the like. If desired the facing material may include a mixture of two or more different types of materials.

Furthermore, the polymeric facing materials may be a sheet of a polymer. For instance, the polymer may be a thermoplastic polymer or a thermoset polymer. In one particular embodiment, the polymeric material may be a thermoplastic polymer. If desired the facing material may include a mixture of two or more different types of polymeric materials. In addition, the polymers may be mixed with other conventional additives to provide the polymeric facing material with the desired properties, for example strength, bond or adhesion strength, water vapor permeability, etc.

Upon sandwiching the gypsum slurry, a forming assembly is utilized to form a continuous length gypsum panel having a desired thickness and width. For instance, forming the continuous length gypsum panel may include passing the gypsum slurry and facing material between a pair of parallel plates or rollers separated from one another by a distance selected to define the thickness of the continuous length gypsum panel. The continuous length gypsum panel is then cut to a desired length with a cutting device thereby providing a gypsum panel.

While on the assembly, the gypsum is allowed to set and hydrate thereby converting from calcium sulfate hemihydrate to calcium sulfate dihydrate in the presence of the water within the slurry. After cutting the gypsum panel, it may then be dried in an oven or kiln to remove any free water (i.e., water not complexed in crystal form or combined with the calcium sulfate during hydration). Upon exiting the oven or kiln, the gypsum panel may then be analyzed and labelled for packaging and distribution.

However, as indicated above, during drying, some of the gypsum may become calcined thereby converting the calcium sulfate dihydrate back to calcium sulfate hemihydrate. This calcination may result in release of the complexed or combined water thereby increasing the total water loss or moisture content (i.e., free water) of the gypsum panel. This calcination may affect the properties and characteristics of the panel. As a result, the present inventors have discovered a method for detecting the degree of calcination and/or moisture content of the gypsum panel, for example inline after drying. In particular, the method and device may allow for either of the aforementioned determinations within a resolution of 25%, such as within 20%, such as within 15%, such as within 10%, such as within 5%, such as within 3%, such as within 1%, such as within 0.5%, such as within 0.3%, such as within 0.1%, such as within 0.05%, such as within 0.01%. That is, such resolution may be in comparison to the actual degree of calcination and/or moisture content, which may be determined using methods known in the art.

Furthermore, in one embodiment, the method may also allow for the determination of the density of the gypsum panel. In particular, the method may allow for the determination in any anomalies in the density of the gypsum panel, such as within the scanning range or area. These anomalies may include, but are not limited to, air pockets, foreign objects (e.g., stones, pebbles, etc.), non-uniform structures, areas of different densities, etc. Such anomalies may have at least one dimension having a size of 1 mm or more, such as 2 mm or more, such as 3 mm or more, such as 5 mm or more. In addition, such non-uniform structure may have fluctuations in the density and/or mechanical structures, which may be observed during a volumetric scanning of the gypsum panel. When present, the non-uniform structure may be present in an amount of 1% or more, such as 5% or more, such as 10% or more of the volume of the gypsum panel.

The principles and operation of a method and a device according to the present invention may be better understood with reference to the figures and the accompanying description.

Figure 1:
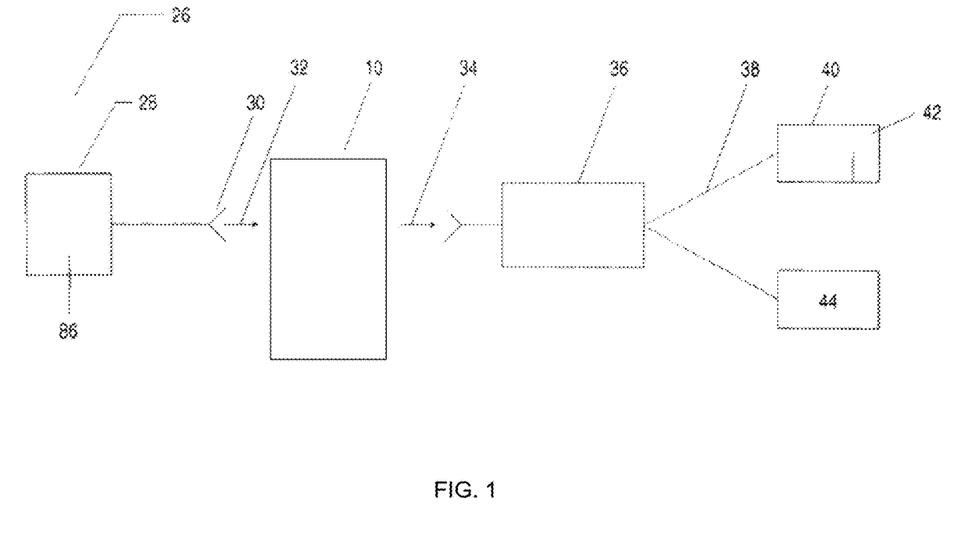
FIG. 1 is a block diagram illustrating one embodiment of a device which can be used with the method of the present invention.

Referring now to the figures, FIG. 1 shows an exemplary device for performing the measurements of the present invention. It should be noted that this device is given for illustrative purposes only and is not meant to be limiting. The device 26 includes a microwave radiation source 28, shown on one side of panel 10. The microwave radiation source 28 preferably includes at least one source antenna 30 for transmitting a source beam 32. The source beam 32 is directed through panel 10 and passes out of panel 10 as an exit beam 34. In this regard, the source beam 32 extends through the panel 10. In particular, in one embodiment, the source beam 32 extends through a thickness (i.e., the smallest dimension) of the gypsum panel 10. The exit beam 34 is received by at least one receiving antenna 36. The receiving antenna 36 is located on a substantially opposing side of panel 10 relative to source antenna 30.

The microwave radiation source 28 may transmit a source beam in one frequency. In another embodiment, transmission may include two frequencies. In a further embodiment, the transmission may include three frequencies. In a further embodiment, the transmission may include four frequencies.

For instance, the one or more frequencies may be within a range of from 10 GHz to 75 GHz. In particular, at least one of the frequencies may be from within the following bands: Ku band of 10-18 GHz, K band of 18-26.5 GHz, Ka band of 26.5-40 GHz, or V band of 40-75 GHz. These bands and frequencies are designated by the Institute of Electrical and Electronics Engineers and thus understood by a person of ordinary skill in the art. If the transmission includes more than one frequency, each frequency may be from a separate band such that the frequencies are not the same. In one embodiment, the transmission may include two frequencies, each having a different value and from a different band. In another embodiment, the transmission may include three frequencies, each having a different value and from a different band. In a further embodiment, the transmission may include four frequencies, each having a different value and from a different band.

Figure 4A:
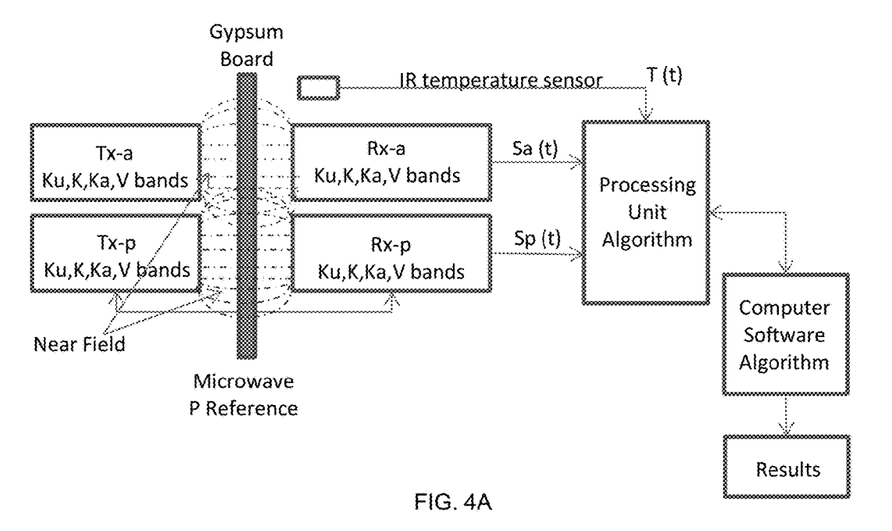
FIGS. 4A-4B are block diagrams illustrating another embodiment of a device which can be used with the method of the present invention.
Figure 4B:
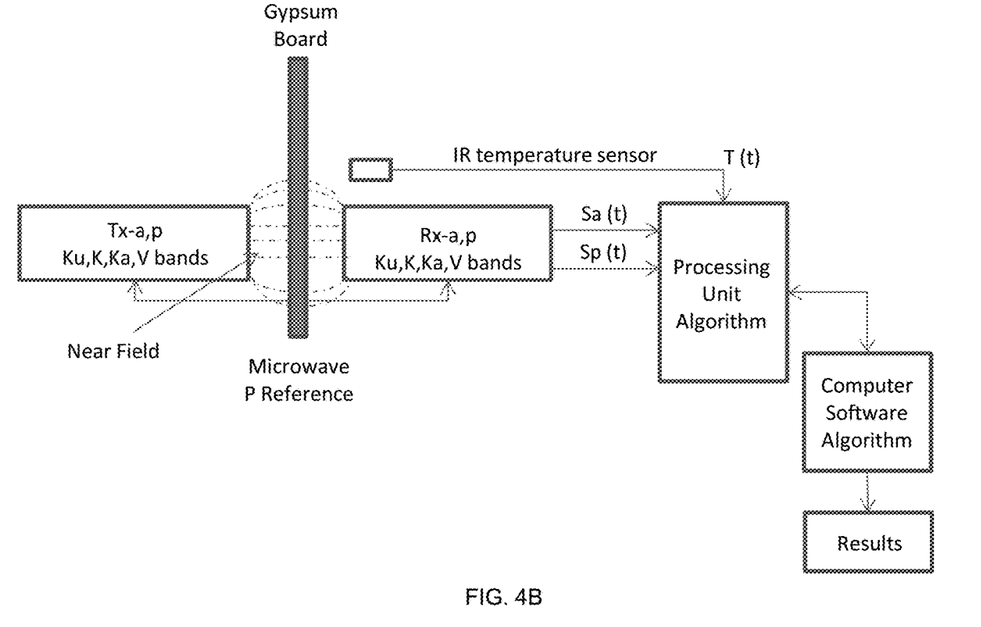

FIG. 1 illustrates one microwave radiation source 28, one source antenna 30, and one receiving antenna 36. However, it should be understood that multiple sets of the aforementioned may be employed. For example, the device may include at least 2, such as at least 3, such as at least 4, such as at least 5, such as at least 6 sets. By having multiple sets, various regions or zones of the gypsum panel can be analyzed and the instruments required may also be relatively smaller in dimension thereby allowing for easier installation and repair, if necessary. As a further example, FIG. 4A illustrates two sources of microwave radiation and two receiving antenna while FIG. 4B illustrates one source of microwave radiation and one receiving antenna.

After receiving antenna 36 has received exit beam 34, receiving antenna 36 produces an antenna signal 38. The antenna signal 38 then goes to an attenuation unit 40. The attenuation unit 40 includes an attenuation measurer 42, which measures the attenuation of antenna signal 38. As source beam 32 passes through panel 10, the source beam 32 is attenuated. The extent of this attenuation is determined by the elementary mass, which is the mass of the panel 10 encountered by source beam 32 and by the moisture content of the panel 10 encountered by source beam 32. Thus, attenuation measurer 42 is actually measuring the extent to which source beam 32 is attenuated by passing through panel 10.

At least a part of antenna signal 38 also goes to a phase shift determiner 44. In addition, the microwave radiation source 28 may also include a reference microwave signal that is connected directly to the phase shift determiner 44. This allows for the determination of the phase shift of the received signal 38. This phase shift is actually the phase shift caused by source beam 32 passing through panel 10, so that the phase shift is the difference between the phase of source beam 32 and the phase of exit beam 34.

Utilizing the attenuation unit 40 and attenuation measurer 42 along with the phase shift determiner 44, the attenuation and the phase shift are then determined. The phase shift may be 250 degrees of less, such as 200 degrees or less, such as 175 degrees or less, such as 150 degrees or less, such as 125 degrees or less, such as 100 degrees or less, such as 75 degrees or less, such as 50 degrees or less, such as 40 degrees or less, such as 30 degrees or less, such as 20 degrees or less, such as 10 degrees or less, such as 5 degrees or less, such as 4 degrees or less, such as 3 degrees or less, such as 2 degrees or less, such as 1 degree or less, such as 0.5 degrees or less, such as 0.3 degrees or less, such as 0.1 degrees or less.

The microwave radiation source 28 can also optionally include a number of features which are designed to maximize the sensitivity of the measurements, by manipulating the direction of the electric field density of source beam 32. The microwave radiation source 28 can include an electric field director 86. The electric field director 86 determines a direction of the electric field density of source beam 32 relative to panel 10, such that the direction of the electric field density partially determines the magnitude of the attenuation and the magnitude of the phase shift. If panel 10 has layers, substantially the maximum attenuation and substantially the maximum phase shift of antenna signal 38 are obtained when the electric field density is substantially perpendicular to the layers of panel 10. When the electric field density is substantially parallel to the layers of panel 10, substantially the minimum attenuation and the minimum phase shift of antenna signal 38 are obtained. Even if panel 10 does not have layers, changing the direction of the electric field density will still alter the attenuation and phase shift of antenna signal 38, according to the orientation of the gypsum panel being measured relative to the electric field density. The electric field director 86 determines the direction of the electric field density according to feedback from attenuation measurer 42. Thus, if the attenuation of antenna signal 38 is low, electric field director 86 can change the direction of the electric field density in order to compensate. Clearly, this has obvious advantages in maximizing the sensitivity and accuracy of the moisture measurements as well as other measurements related to the panel characteristics (e.g., density).

Figure 2:
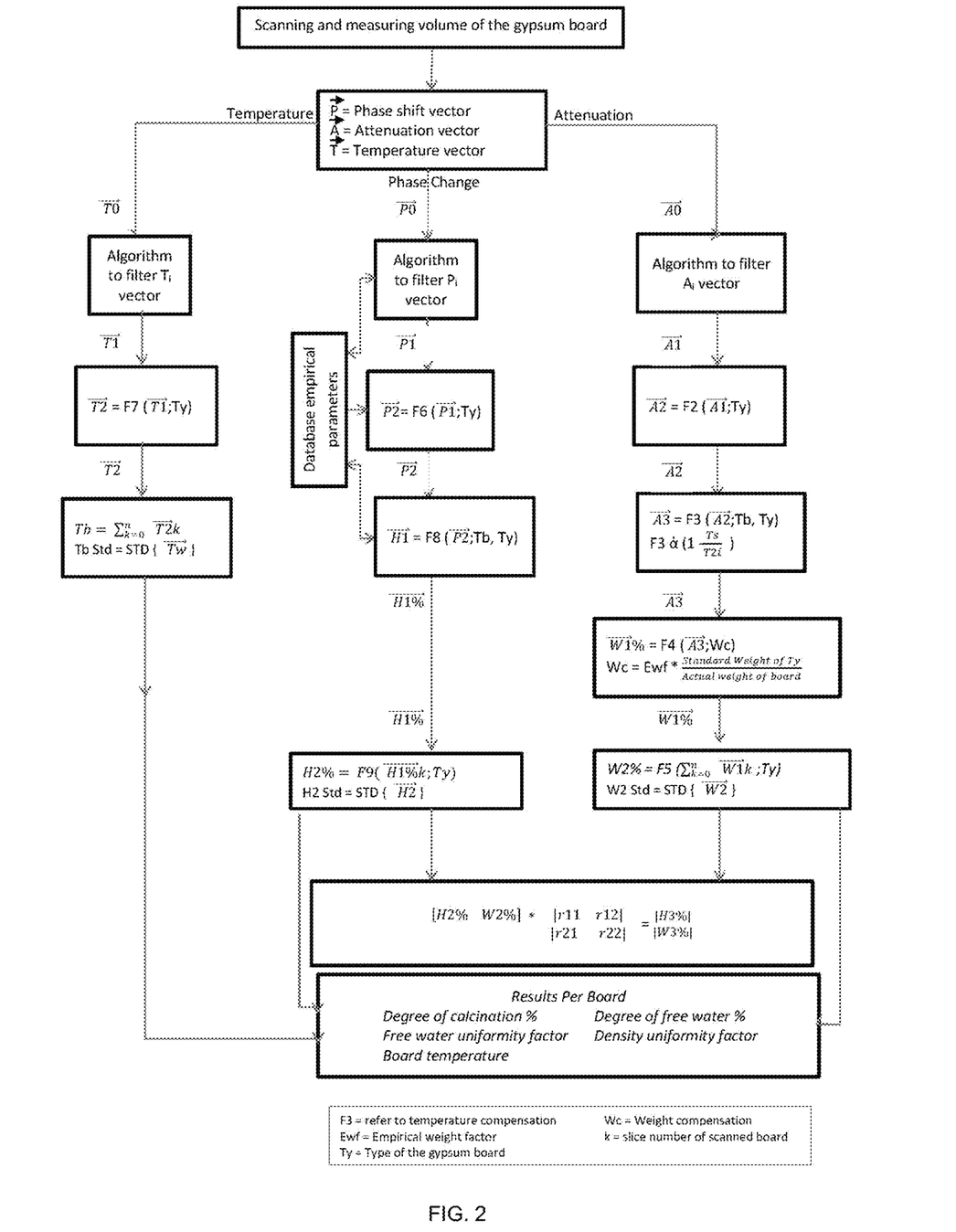
FIG. 2 is a flow chart of the method of calculating the density, degree of calcination, and/or moisture content of a gypsum panel.

The attenuation and the phase shift of antenna signal 38 are then used to determine the calcination, the moisture content, and/or density variance of panel 10. FIG. 2 shows an example of a flow chart of the calculations for determining the calcination and/or moisture content and the internal structure of the panel. The attenuation is generally used to determine the moisture content of the gypsum panel, while the phase shift is generally used to determine the internal structure of the gypsum panel. The method and device are generally capable of determining the difference between free water and the combined or crystal water based on the vibration energy of each thereby allowing for determination of the moisture content (e.g., free water). Both the attenuation and the phase shift are used in combination with empirically determined correction factors to calculate the calcination and/or final moisture content of the gypsum panel. The final moisture content comprises a final free moisture content and a final crystal moisture content wherein the free moisture (or water) content and the crystal moisture (or water) content is as defined herein. Furthermore, the determination of the final moisture content may allow for determination of each of the final free moisture (or water) content and the final crystal moisture (or water) content As further clarification, the moisture or water associated with a gypsum board can be considered either free water or combined or crystal water. For example, the free water is any water that is standalone water within the gypsum board. Meanwhile, the combined or crystal water is the water that is contained in the crystals, such as the gypsum crystals. In this regard, such combined or crystal water is partially or completely lost or removed during calcination. The system and method described herein are capable of distinguishing between the crystal water and the free water in order to determine the water content of the gypsum board.

The first step in the flow chart is the scanning of the gypsum panel, which can be performed using the device essentially as described above. In addition, the volume of the gypsum panel can also be determined. The gypsum panel is scanned by transmitting a plurality of microwaves through the panel so that they pass through the panel and are received on the other side. From this scanning step, the phase shift, attenuation, and temperature are determined. In this regard, the flow chart now branches into three parts. The right branch shows the steps used in determining the raw moisture content (and/or anomalies detection in density) of the gypsum panel, while the middle branch shows the steps used in determining the internal structure of the gypsum panel, while the left branch shows the steps used in determining the temperature of the gypsum panel. The raw moisture content comprises a raw free moisture content and a raw crystal moisture content wherein the free moisture (or water) content and the crystal moisture (or water) content is as defined herein. Furthermore, the determination of the raw moisture content may allow for determination of each of the raw free moisture (or water) content and the raw crystal moisture (or water) content.

Following the right branch, first an algorithm is used to filter the data points obtained for the attenuation. Each time a measurement of the attenuation is made as described above in FIG. 1, a data point is obtained. These data points must be filtered since otherwise artefactual data could be obtained.

Once the data has been filtered, the attenuation is corrected for the effect of the temperature of the panel, to produce a temperature-corrected attenuation value. The function for this correction is proportional to $I-T_s/T_e$, where $T_s$ is the standard temperature and $T_e$ is the measured temperature. The temperature-corrected attenuation value thus is compensated for the effect of measurements at different temperatures. Next, the temperature-corrected attenuation value is corrected for weight, to produce a weight-corrected attenuation value. In addition, it should be understood that these steps are optional steps and may not be necessary. For example, they may not be required for real time volumetric scanning and calculation of the estimated moisture content (A value) and estimated calcination (P value) of the gypsum panel. Also, the T value can be calculated from Ti (wherein i is the index of the temperature vector and i=1 . . . N wherein N=number of vector points).

Next, in another optional step, the complete set of all weight-corrected attenuation values from a single slice of gypsum panel is used to calculate a raw moisture value for that slice. This calculation is performed according to a function which can be a linear integration of all the weight-corrected attenuation values or else a polynomial, depending upon such empirical factors as the type of gypsum panel being measured, the shape and structure of the panel itself. In any case, these empirical factors are included in the calculation, so that their effects on the measurement can be compensated for. This raw calcination and/or moisture value will be used in the determination of the final calcination and/or moisture value for the slice of gypsum panel. However, the final calcination and/or moisture value cannot be determined without knowing the density of gypsum panel, which can be calculated based on the phase shift.

In this regard, the middle branch of FIG. 2 provides the flowchart for determining the phase shift and calculating the density of the gypsum panel, in accordance with empirical information from a database. The empirical information includes the type of gypsum panel and the structure of the panel itself, as well as the location of the panel relative to the antenna and transmitter.

Additionally, the database preferably contains "fuzzy descriptors" which are used to find the correct phase region and to determine the proper relationship between the measured phase shift values and the calculated density values. These "fuzzy descriptors" are obtained by collecting phase shift data from an analysis of a test shape having known features, and then comparing the calculated density values with the true, known density values of the test shape. From this analysis of the test shape, the proper correlation between the measured phase shift values and the calculated density values can be determined. Since this correlation depends upon both the structure and geometry of the test shape, and upon the material or materials from which the test shape is constructed, such an analysis must be performed for substantially every desired shape and material in order to obtain these essentially empirical correlations.

Any deviation of the measured density of the slice of gypsum panel from the previous measurement of the density of the previous slice is determined. Such deviations are important because they reveal irregularities in the internal structure of the gypsum panel. Because such sources of deviations as the presence or absence of a hollow core in the measured slice have already been compensated for, the only remaining source of a deviation is irregularities in the internal structure of the gypsum panel.

Next, the true density variance of gypsum panel is calculated in one of two different ways, depending, upon deviations in the calculated density variance when comparisons are made between two or more slices. In the first method, the deviation or variance in the calculated density between a plurality of slices is relatively small, such that a single density variance value can be used for all subsequent calculations. Alternatively, the deviation between the calculated densities of a plurality of slices is relatively large, such that a plurality of density values, preferably all density values, are used for the subsequent calculations. The estimation of the calcination, P value, can be based on $P_i$ (wherein i is the index of the phase shift vector and i=1 . . . N wherein N=number of vector points).

Finally, the panel density variance value or values, and the raw calcination and/or moisture value, are combined to determine the true calcination and/or moisture value. The equation for calculating the true calcination and/or moisture value includes both the density variances and any deviations in the calculated anomalies (both of density variances and moisture variances) within the whole slice, as well as an empirically determined correlation factor. The correlation factor depends upon the type and structure of gypsum panel and was empirically determined through experimentation. The true moisture value is then output, for example by displaying on a display unit which could include a video screen or by other devices for displaying the information. Preferably, any deviations in the internal structure of the gypsum panel which were found by comparison of the measured phase shifts are also displayed, because such information can be very important to the manufacturer or processor of the gypsum panel.

The gross phase shift difference between two phase shifts measured after microwave radiation of two different frequencies has been transmitted through the gypsum panel can be described as follows.

$$\Delta P(gross) = F_2/(F_2 - F_1) * (P_2 - P_1)$$

The final phase shift difference is:

$$\Delta P(final) = P_i + P_g \bmod(\pi)$$

Thus, the gross phase shift difference is obtained by sequentially transmitting microwave radiation of at least two different frequencies and "hopping" or alternating at least between these two frequencies at each point in the gypsum panel.

The equations which describe the phase shift and attenuation are as follows.

1. $\lambda = C/F$;
   $l$ = (path length of radiation)$\varepsilon'$ = (dielectric constant of material)

2. $P_1 = \dfrac{2\pi}{\lambda_1}\sqrt{\varepsilon'}\, l$;

3. $P_1 = \dfrac{2\pi}{\lambda_2}\sqrt{\varepsilon'}\, l$;

4. $P_1 = KF_1; P_2 = KF_2; K = \dfrac{2\pi}{C}\sqrt{\varepsilon'}\, l; P_1 - P_2 = \Delta P = K(F_1 - F_2)$;

5. $P_1 = Ph_{(t)}(F_1); P_2 = Ph_{(t)}(F_2)$;

6. $K = \dfrac{P_1 - P_2}{F_1 - F_2}; (F_1 > F_2)$

7. $Pg$ = (phase including $n\pi$ term) = $K \cdot F_i (i$ is 1 or 2)

8. Corrected Phase-shift = $(Pg - n\pi) + \dfrac{P_1 - P_2}{2}; n = (Pg - n\pi > 0)$ Note that F is the frequency of the microwave radiation; I is the length of the beam path as it passes through the gypsum panel; $\varepsilon'$ is the dielectric constant of the bulk of gypsum panel; $P_1$ is the phase deviation for microwave radiation at frequency $F_1$; $P_2$ is the phase deviation for microwave radiation at frequency $F_2$; $K(F_1-F_2)$ is the difference between the phase deviation of the radiation at frequencies $F_1$ and $F_2$; $P_h(t)$ is the true phase shift, such that the measured phase shift, $P_1$, is a function of the true phase shift and of the frequency $F_1$, for example; Pg is the gross phase shift difference; and n is the largest number which satisfies equation 8 such that Pg-n$\pi$ is greater than 0.

Although these equations both describe the corrected phase shift and can be used for its calculation, the refinements of the calculations must be done according to empirically observed properties of the gypsum panel itself and effects of the surrounding environment. These empirically-based calculations may be conducted according to the following steps.

In step 1, a plurality of frequencies of microwave radiation is sequentially transmitted through the gypsum panel. In step 2, the attenuation and the corrected phase shift are calculated for the plurality of frequencies of microwave radiation. In step 3, an algorithm is performed to filter noise from the calculated values of the attenuation and the corrected phase shift. The attenuation for a frequency $F_{2i}$ can be described as $A_{2i} = a_1 A_{1i} + b_1$. Similarly, the phase shift is $P_{i2} = a_2 P_{1i} + b_2$. Note that $A_{1i}$ and $P_{1i}$ are the attenuation and phase shift values obtained from the previously measured frequency EH. The values for $a_1$, $a_2$, $b_1$ and $b_2$ are taken from a database, depending upon the particular application and gypsum panel. Examples of relative values to the phase shift of the microwave path through the board may be from 10 degrees to 280 degrees function of gypsum board types. For example, the P value for a ¼ inch board can be between 0.155 to 0.3 (phase shift of 20 to 35 degrees), for a ½ inch board can be from 0.3 to 0.51 (phase shift of 40 to 80 degrees), for a ⅝ inch board can be from 0.5 to 0.7 (phase shift of 60 to 120 degrees), and for a 1 inch board can be from 0.8 to 1.2 (phase shift of 100 to 200 degrees). In this regard, the values for a; may be {1,5,10} and $b_i$ may be {0,0.1,0.5,1,5,10}. The parameters can be used based on the type of boards and the P values range that are required to be display.

| Type | P0 values from | P0 values till | Params. values P1 values from | Pa = 2 Pb = 1 P1 values till | Phase Shift till | Phase Shift From |
|---|---|---|---|---|---|---|
| 0.25 | 0.15 | 0.35 | 1.3 | 1.7 | 20.25 | 47.25 |
| 0.5 | 0.3 | 0.6 | 1.6 | 2.2 | 40.5 | 81 |
| 0.625 | 0.45 | 0.85 | 1.9 | 2.7 | 60.75 | 114.75 |
| 1 | 0.7 | 1.3 | 2.4 | 3.6 | 94.5 | 175.5 |

In particular, for a ¼ inch board, the P0 values may range from 0.15 to 0.35 and the P1 values may range from 1.3 to 1.7. In this regard, the phase shift may be from 20.25 to 47.25 degrees. For a ½ inch board, the P0 values may range from 0.3 to 0.6 and the P1 values may range from 1.6 to 2.2. In this regard, the phase shift may be from 40.5 to 81 degrees. Also, for a ⅝ inch board, the P0 values may range from 0.45 to 0.85 and the P1 values may range from 1.9 to 2.7. In this regard, the phase shift may be from 60.75 to 114.75 degrees. Further, for a 1 inch board, the P0 values may range from 0.7 to 1.3 and the P1 values may range from 2.4 to 3.6. In this regard, the phase shift may be from 94.5 to 175.5 degrees.

Furthermore, as indicated herein, the P0 values are the base value signals, such as those from a scanner (e.g., microwave scanner). The P1 values are the values after processing the vectors and matrix using the empiric calculations as disclosed herein. Also, the Pa and Pb values are used to present the results of the P1 values in ranges suitable to users.

These values are empirically determined based upon empiric measurements. This calculation to filter noise is preferably performed upon all calculated values of the attenuation and the corrected phase shift. In addition, the value of each of the plurality of frequencies is used for these calculations, because the attenuation and phase shift values are as said also dependent upon the frequency of the microwave radiation.

Preferably, any "edge" measurements, or measurements made when an edge of the panel was passing through the beam of microwave radiation, are eliminated from any subsequent calculations because these measurements are artefactual. The determination of whether a particular measurement is an "edge" measurement can be made in a number of ways. For example, the location of the panel relative to the beam can be determined, such that when an edge of the panel is about to pass through the beam, a signal can be sent to the attenuation and phase shift determiners. Alternatively and preferably, the measurement of the attenuation can be plotted, and any artefactually high peaks or low troughs of attenuation can be eliminated, for example by removing any values which are more than two or three standard deviation from the average attenuation. Thus, any artefactual "edge" measurements are preferably eliminated at this stage of the analysis.

In step 4, the density, the calcination, and the moisture content of the panel are calculated from the plurality of filtered attenuation and filtered phase shift values, preferably from all of these values. The moisture content of the gypsum panel is determined from the following equation:

$$W\% = a_0 + \sum_{i=1}^{n}(A_i * r_i).$$

The calcination of the gypsum panel can be determined from the following equation:

$$H\% = b_0 + \sum_{i=1}^{n}(P_i * k_i).$$

In the aforementioned, $r_i$ is the A vector factor described previously, $k_i$ is the P vector factors, and $a_0$ and $b_0$ are the bias of the W and H that might need to be added based on the gypsum panel. The term $W_i$ is a function of the attenuation $A_2$ and the $P_i$ is the phase shift $P_2$ as determined in step 3, as well as of the type and structure of gypsum panel. The term $W_i$ is a function of the attenuation $A_2$ and the phase shift $P_2$ as determined in step 3, as well as of the type and structure of gypsum panel. The correlation factor is obtained from a database of these values, determined from empiric observation.

The density of the gypsum panel is then calculated from a statistical function of the sum of the phase shift values, again taken from the database. This function depends upon the characteristics of the gypsum panel being analyzed, as for the calculation to filter noise described for step 3. Also, the density variance is a function of both $P_2$ as determined in step 3 and the type and structure of the gypsum panel. Thus, the necessary information is taken from a database of empirically determined information.

Preferably, at this stage any defects in the gypsum panel are detected by examining the densities collected for a portion of the gypsum panel. The defect could include an irregular moisture distribution within the interior of the gypsum panel, such as an unusually high moisture content within the gypsum panel, or the presence of a foreign body inside the gypsum panel. The defect could include an irregular calcination distribution within the interior of the gypsum panel, such as an unusually high calcination within the gypsum panel.

In step 5, the temperature of the gypsum panel is preferably compensated for in the determination of the calcination, moisture content, and density, if necessary. Again, the necessity for step 5 is determined at least partially according to empiric observations.

In step 6, the calcination, the moisture content, and the density of the gypsum panel are output, for example to a display on a computer screen or by printing onto paper. The advantages of determining the calcination, the moisture content, and the density of each point in a gypsum panel at more than one frequency of microwave radiation are as follows. First, measuring the attenuation and phase shift at one point in the gypsum panel but with more than one frequency permits averaging of the values to obtain a more accurate result. Second, the change in the attenuation is linear, so that alterations in the attenuation due to the measurement at different frequencies can be easily calculated. Any remaining differences are then removed by averaging. Third, a good range of frequencies for any particular type or form of gypsum panel can be selected, rather than relying upon a single frequency. Finally, measurements at the chosen range of frequencies also enable the true phase shift to be determined.

The third point, the ability to choose a good range of frequencies for a particular type or form of gypsum panel, is particularly important for mixed materials, or materials containing more than one type of substance. Additionally, this mixture of different types of materials with different properties causes harmonics to appear in the transmitted microwaves. However, the true phase shift can be determined from a linear portion of the curve of phase shift plotted against frequency. Thus, using a plurality of frequencies can simplify the determination of the phase shift for mixed materials.

Optionally and preferably, a frequency range of microwave radiation can be chosen which minimizes reflection of radiation from the gypsum panel and maximizes transmission of microwave radiation through the gypsum panel. More preferably, a range of suitable frequencies is chosen from a database before the measurements are made. The choice of a particular range is empirically based on such factors as the type of gypsum panel and the structure of gypsum panel. As the measurements are made, the frequency range can also be selected to reduce or eliminate ambient noise from environmental interference. An example of such interference could be a cellular phone for example. Preferably, more than one frequency range is examined before selecting a particular range in which to make the measurements, in order to reduce or eliminate this problem.

In addition, preferably adjustments are made to the selected range of frequencies, such that more measurements are made within a smaller range of frequencies which gives the best results. Thus, adjustments to the frequency range made "on the fly" enable the most sensitive and accurate measurements to be made.

In this regard, the frequencies utilized may include super high frequency (SHF) and/or extremely high frequency (EHF). Generally, super high frequency includes a frequency range of 3 GHz to 30 GHz while extremely high frequency includes a frequency range of from 30 GHz to 300 GHz. While that may be the case, the present invention and method may utilize even more specific frequencies within these ranges. Generally, the present invention and method may utilize at least one frequency within the following bands as defined below: Ku band, K band, Ka band, or V band. In particular, the Ku band includes frequencies from 10 GHz to 18 GHz, the K band includes frequencies from 18

GHz to 26.5 GHz, the Ka band includes frequencies from 26.5 GHz to 40 GHz, and the V band includes frequencies from 40 GHz to 75 GHz. However, when utilizing multiple frequencies, the present invention and method may utilize at least two, such as at least three, such as at least four different frequencies. In this regard, these frequencies may be from at least two, such as at least three, such as at least four of the aforementioned bands.

Figure 3:
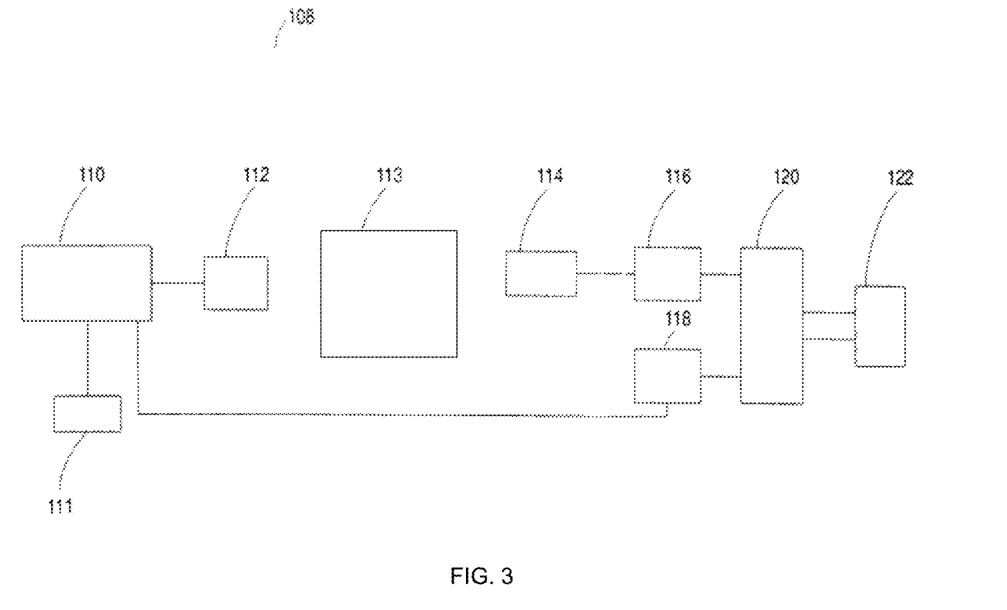
FIG. 3 is a block diagram illustrating another embodiment of a device which can be used with the method of the present invention.

FIG. 3 shows a schematic diagram of another preferred embodiment of the present invention, in which the device of FIG. 1 has been adjusted to permit transmission of more than one frequency of microwave radiation. In particular, a multiple-frequency system 108 has a multiple-frequency transmitter 110 for sequentially transmitting microwave radiation at a plurality of frequencies. The frequency to be transmitted is selected by a frequency controller 112. The transmitter 110 then causes a transmitting antenna 112 to transmit microwave radiation at the desired frequency. The transmitted microwave radiation then passes through gypsum panel 113 and is received by a receiving antenna 114. The receiving antenna 114 sends a signal to a signal receiver 116. The signal receiver 116 may be a hetrodyne receiver. Substantially simultaneously, a reference signal is sent from transmitter 110 to a reference receiver 118, which also may be a hetrodyne receiver. The signal receiver 116 sends a measurement signal (labelled as "I.F. 1") to a detector 120, while reference receiver 118 sends a reference signal (labelled as "I.F. 2") to detector 120. The detector 120 uses the reference signal to determine the correct attenuation of the measurement signal and then passes both signals to a phase detector 122, which determines the correct phase shift for the measurement signal.

As indicated above, the present invention allows for determining the degree of calcination of the gypsum panel upon drying. In this regard, if it is determined that the extent of calcination is greater than desired, remedial action may be utilized. For example, the drying temperature of the panels in the kilns may be reduced. The drying temperature may be changed throughout all zones or in certain zones. Alternatively or in addition, the drying time of the panels in the kilns may be decreased. Accordingly, the line speed may be adjusted. In addition, the position of the dampers may be adjusted to optimize air flow in one zone or multiple zones. Furthermore, the wet end formulation may be adjusted. Regardless, the remedial action may be one that is utilized for optimizing the drying profile. In one embodiment, remedial action may be taken if the calcination as determined according to the method disclosed herein was 5% or more, such as 8% or more, such as 10% or more, such as 12% or more, such as 15% or more.

EXAMPLES

Figure 5:
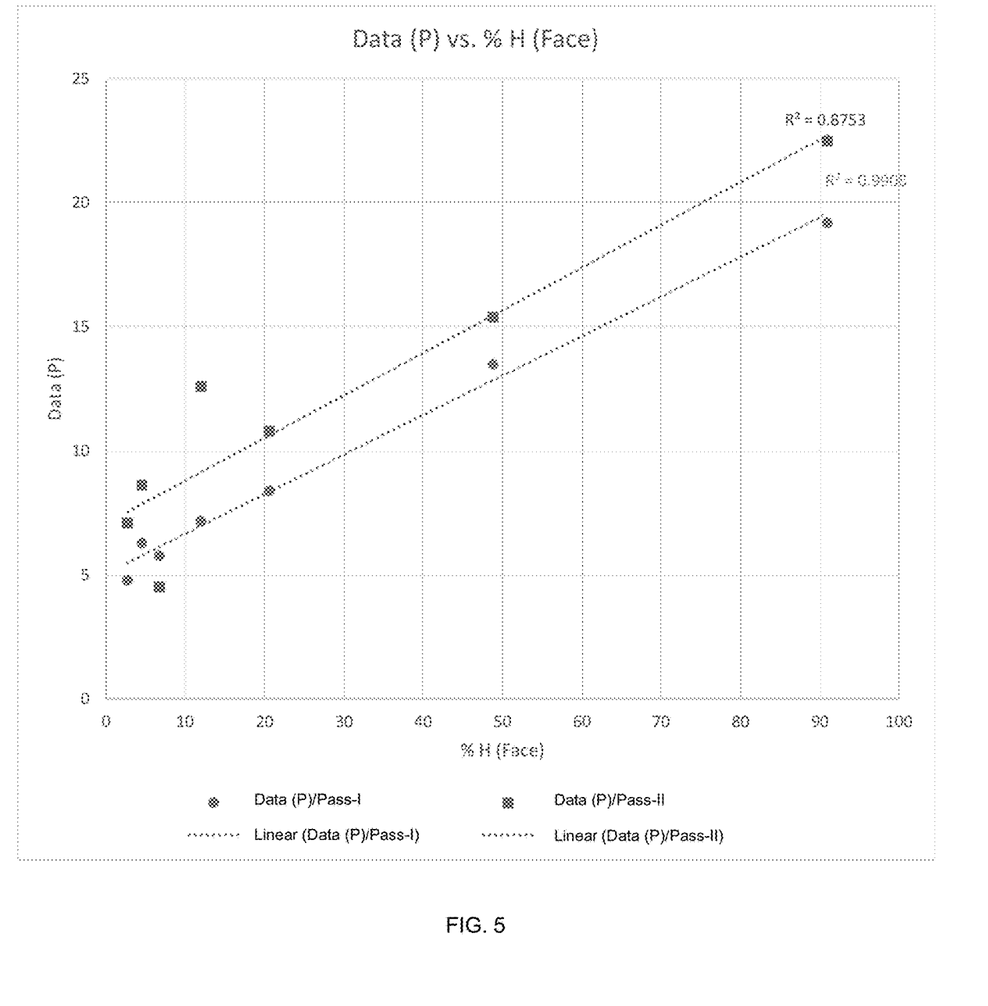
FIGS. 5-7 illustrate the correlation between the actual calcination and the data generated for the P value according to the present method.
Figure 6:
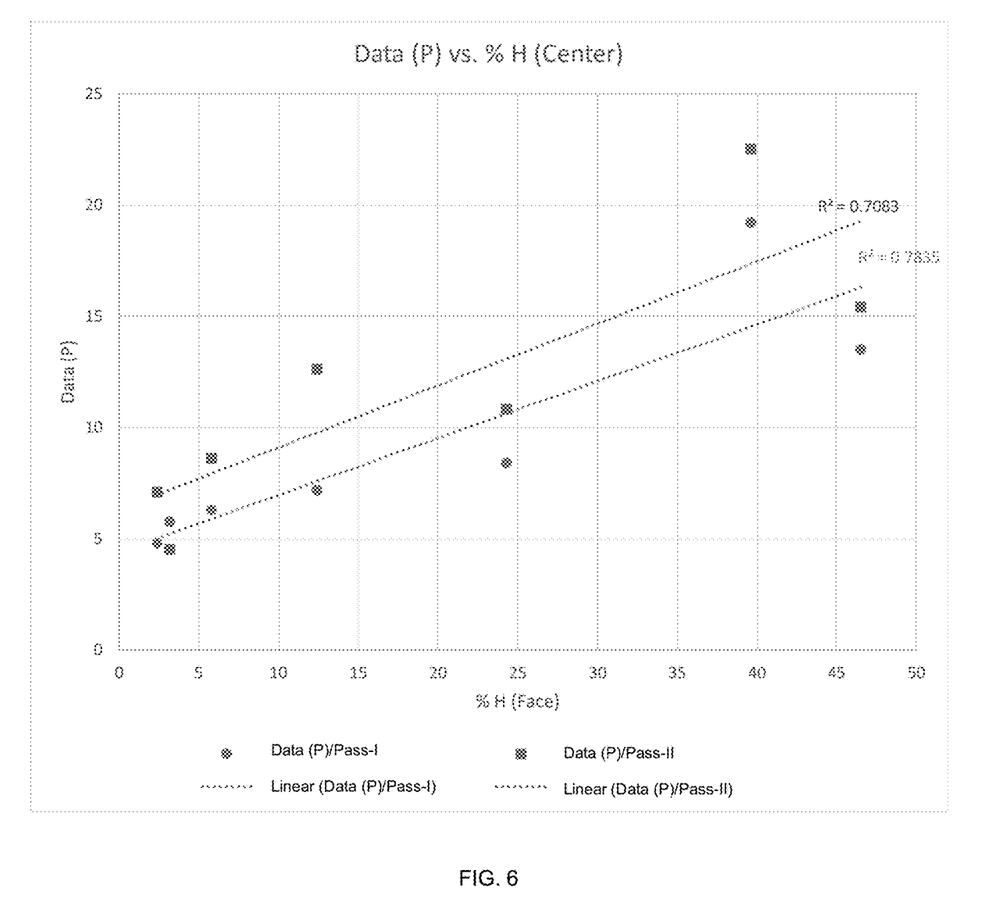
Figure 7:
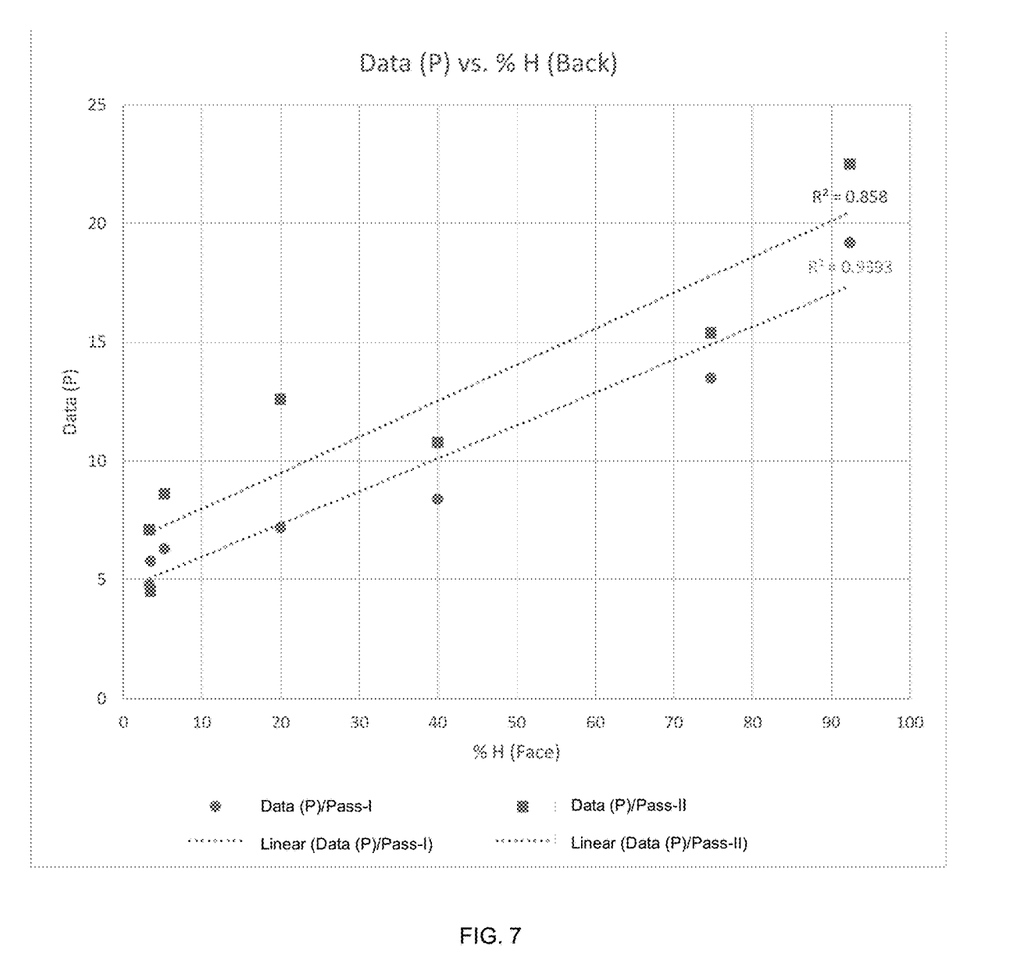
Figure 8:
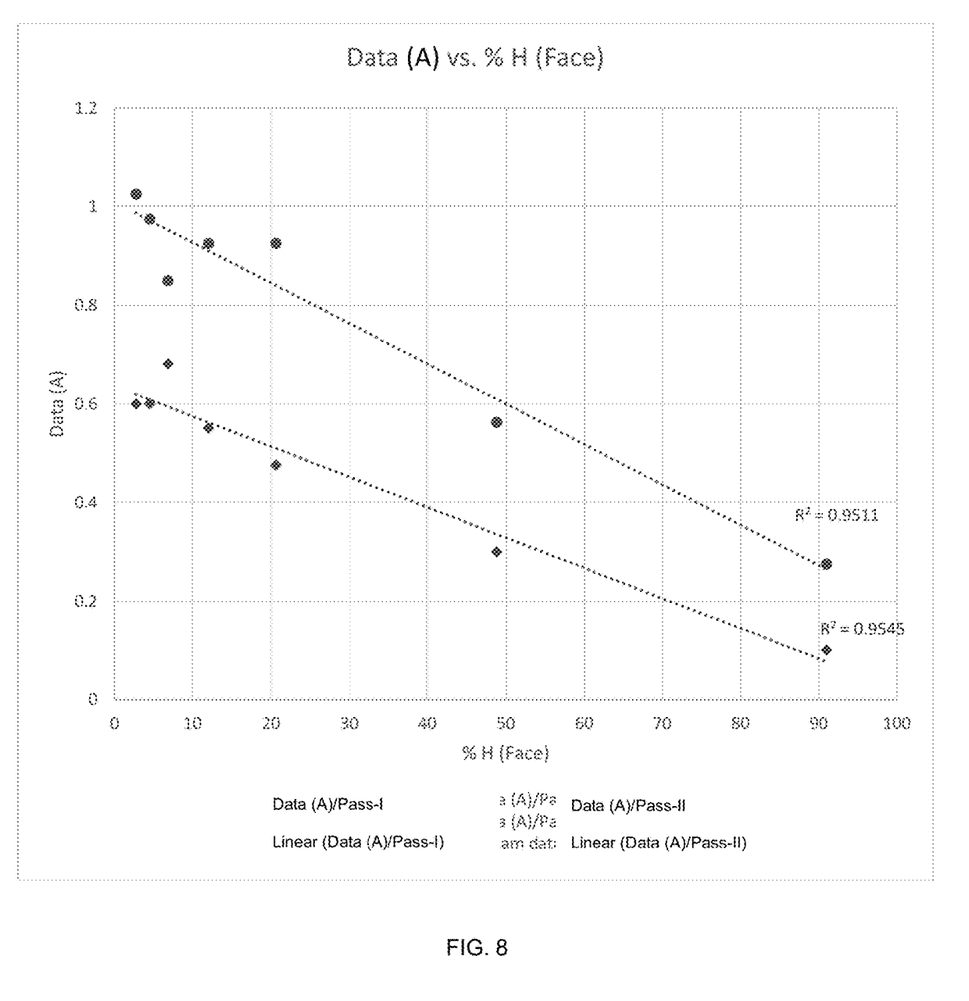
FIGS. 8-10 illustrate the correlation between the actual calcination and the data generated for the A value according to the present method.
Figure 9:
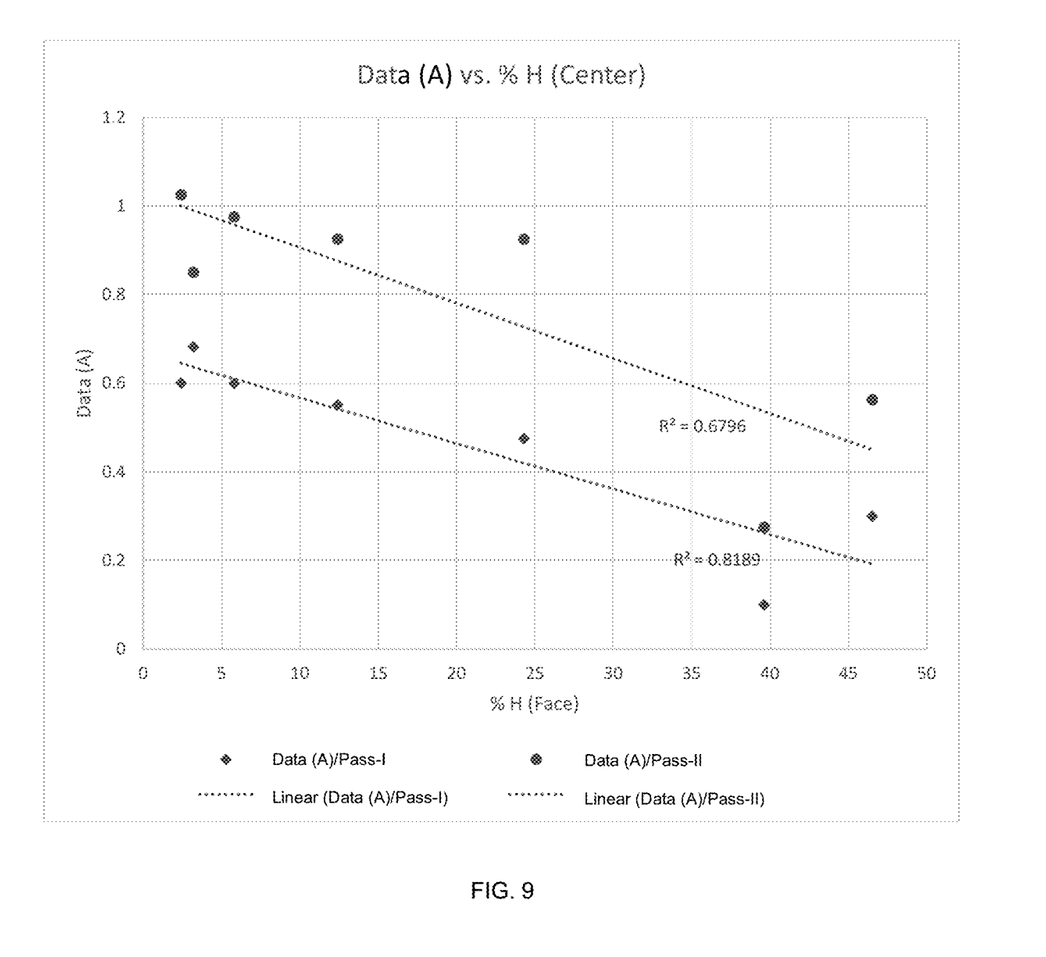
Figure 10:
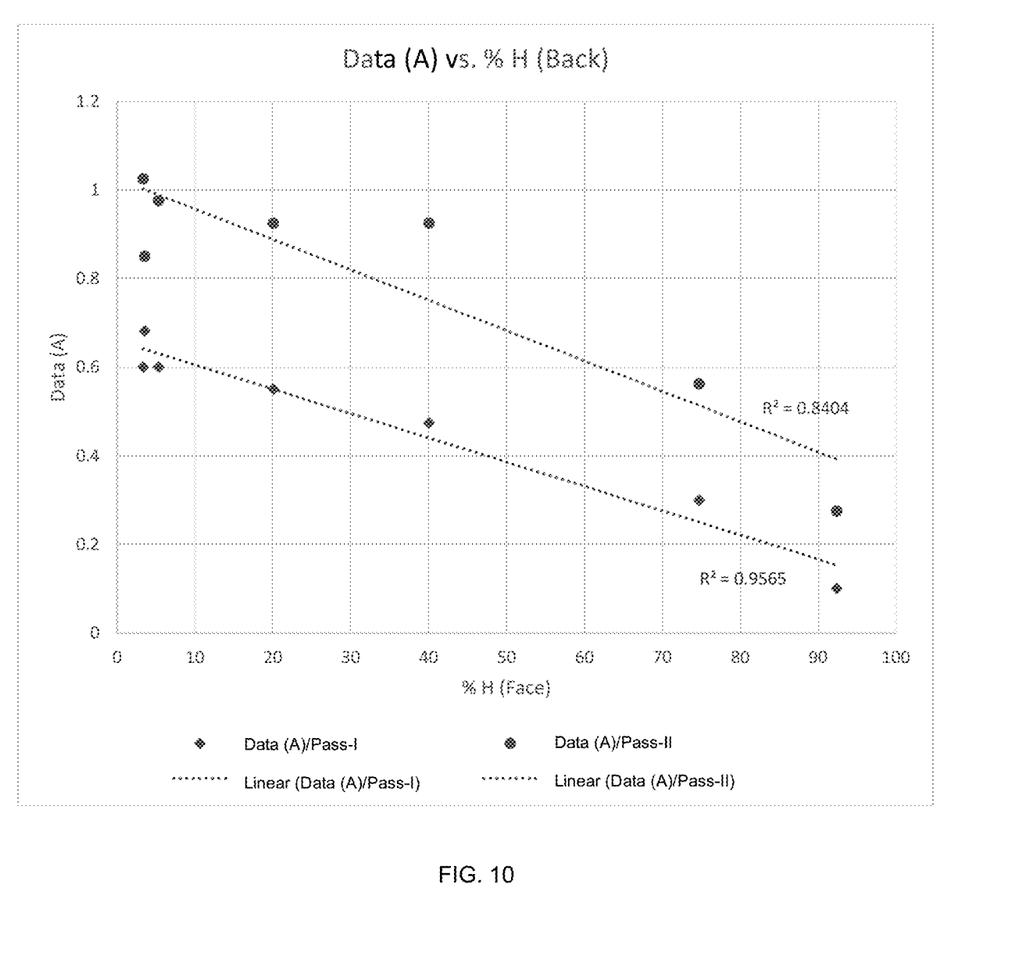

Various gypsum panels were calcined to a certain degree. FIGS. 5-7 (P value) and FIGS. 8-10 (A value) illustrate the correlation between the actual calcination and the data generated according to the present method. The degree of calcination was determined on the face of the panel, the back of the panel, and the center of the panel. In particular, the actual degree of calcination was determined by a calibration curve prepared in advance. The amount of the calcium sulfate hemihydrate or calcium sulfate dihydrate was calculated by XRD and was plotted vs. the P value or the A value. As seen in the figures, the correlation value was relatively high.

As indicated by the data and figures, the present invention and method demonstrate a good correlation between the P value and the degree calcination as well as the A value and the degree of calcination.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

The invention claimed is:

1. A method of determining a free moisture content and/or a degree of calcination of a gypsum panel comprising a gypsum core, a first sheet of facing material, and a second sheet of facing material wherein the first sheet of facing material and the second sheet of facing material sandwich the gypsum core, the method comprising:
   (a) transmitting a microwave beam through at least a first portion of the gypsum panel, such that the microwave beam is a transmitted microwave beam;
   (b) receiving the transmitted microwave beam to form a received microwave beam;
   (c) determining a phase shift and an attenuation from the received microwave beam;
   (d) repeating steps (a) to (c) for at least a second portion of the gypsum panel, such that a plurality of phase shifts and a plurality of attenuations is obtained;
   (e) using at least one empirical factor to correct the plurality of attenuations, producing a plurality of corrected attenuations;
   (f) calculating a raw moisture content of the gypsum panel from the corrected attenuations wherein the raw moisture content comprises a raw free moisture content and a raw crystal moisture content;
   (g) using a calibration factor to correct the plurality of phase shifts, producing a plurality of corrected phase shifts; and
   (i) calculating a final moisture content of the gypsum panel wherein the final moisture content comprises a final free moisture content and a final crystal moisture content.

2. The method according to claim 1, wherein the method is conducted inline during the process of making the gypsum panel.

3. The method according to claim 2, wherein the method is conducted after drying the gypsum panel and before packaging the gypsum panel.

4. The method according to claim 1, wherein the method is conducted offline from the process of making the gypsum panel.

5. The method according to claim 1, wherein the moisture content is within 25% of the actual moisture content.

6. The method according to claim 1, wherein the microwave beam includes only one frequency.

7. The method according to claim 1, wherein the microwave beam includes at least two frequencies.

8. The method according to claim 1, wherein the microwave beam includes one or more frequencies within a range of from 10 GHz to 75 GHz.

9. The method according to claim 1, wherein the gypsum panel features an irregularity in a density calculated by comparing one of the plurality of corrected phase shifts to a previous value of the corrected phase shifts, such that the irregularity is detected if one of the plurality of corrected phase shifts differs from the previous value.

10. The method according to claim 1, wherein the corrected attenuations and the corrected phase shifts are further corrected by removing attenuations and phase shifts produced after the microwave beam passes through an edge of the gypsum panel, such that a first portion of the microwave beam passes through the portion of the gypsum panel and a second portion of the microwave beam substantially does not pass through the portion of the gypsum panel.

11. The method according to claim 1, the method further comprising determining a density of the gypsum panel, wherein the step of determining the density includes detecting a defect in the gypsum panel.

12. The method according to claim 6, wherein the defect includes the presence of a foreign body inside the gypsum panel.

13. The method according to claim 1, wherein the at least one empirical factor is a plurality of empirical factors comprising the weight of the gypsum panel, the type of the gypsum panel, or a combination thereof.

14. The method according to claim 1, wherein the plurality of corrected attenuations is further corrected by removing attenuations produced after the microwave beam passes through at least a portion of the gypsum panel.

15. The method according to claim 1, wherein the gypsum panel comprises calcium sulfate dihydrate.

16. The method according to claim 1, wherein the method further comprises a step of undertaking remedial action after determining the moisture content.

* * * * *